US005498427A

United States Patent [19]

Menasche

[11] Patent Number: 5,498,427
[45] Date of Patent: Mar. 12, 1996

[54] SOLUTIONS FOR THE PERFUSION, PRESERVATION AND REPERFUSION OF ORGANS

[75] Inventor: Philippe Menasche, Paris, France

[73] Assignee: Pasteur Merieux Serums et Vaccines, Lyon, France

[21] Appl. No.: 300,210

[22] Filed: Aug. 18, 1994

Related U.S. Application Data

[63] Continuation of Ser. No. 946,073, Sep. 18, 1992, abandoned, which is a continuation-in-part of Ser. No. 794,878, Nov. 19, 1991, abandoned.

[30] Foreign Application Priority Data

Nov. 20, 1990 [FR] France .................................. 90 14424
Jul. 17, 1991 [FR] France .................................. 91 09027

[51] Int. Cl.$^6$ .......................... A61K 33/14; A61K 33/06; A61K 38/00; A61K 31/70; A61K 31/415; A61K 31/95

[52] U.S. Cl. .......................... 424/678; 424/679; 424/681; 424/682; 514/2; 514/23; 514/25; 514/385; 514/561

[58] Field of Search ...................... 514/562, 563, 514/564, 2, 23, 385, 25, 561; 424/678, 679, 681, 682

[56] References Cited

U.S. PATENT DOCUMENTS 4,877,810  10/1989  Mickle ..................... 514/456
5,095,027  3/1992  Goldberg ................. 514/369

FOREIGN PATENT DOCUMENTS

88/05044  7/1988  WIPO ................. C02D 211/94

OTHER PUBLICATIONS

Astier et al; "Instability of Reduced Glutathione in Commercial Belzer Cold Storage Solution"; The Lancet, pp. 556–557; Sep. 2, 1989.
Wicomb et al; "The Role of Reduced Glutathione in Heart Preservation . . . "; Transplantation J4 (1) Jul. 1992, pp. 181–182.

Standeven et al, "Cold-blood potassium cardioplegia", J. Thorac Cardiovasc. Surg., 78:893–907, 1979.
Bernier et al, "Reperfusion-induced Arrhythmias and Oxygen-derived Free Radicals", American Hear Association, vol. 58, No. 3, pp. 331–340, Mar. 1986.
Chatham, et al, "Depletion of myocardial glutathione: its effects on heart function and metabolism during ischaemia and reperfusion", Cardiovascular Research, 22, pp. 833–839, 1986.
Blaustein, et al, "Myocardial Glutathione Depletion Impairs Recovery After Short Periods of Ischemia", Circulation, vol. 80, No. 5, pp. 1449–1457, Nov. 1989.
Singh et al, "Relation Between Myocardial Glutathione Content and Extend of Ischemia–Reperfusion Injury", Circulation, vol. 80, No. 6, pp. 1795–1803, Dec. 1989.
Wicomb et al, "Role of Glutathione in 24–Hour Heart Storage by Microperfusion (MP) Using a New Polyethylene Glycol Solution", Journ. of Molecular and Cellular Cardiology, vol. 22, Supplement V, 1990.
Kantamneni, et al, "Extended Preservation of Canine Myocardium Using UW Solution", Dept. of Surgery, University of Wisconsin, Madison, Wisconsin, 1987.
Forman et al, "Glutathione Redox Pathway and Reperfusion Injury", Circulation, vol. 78, No. 1, pp. 202–213, Jul. 1988.
Menasche et al, "Les Piegeurs de Radicaux Libres dans la Protection Myocardique en Chirurgie Cardiaque", Ann de Cardiologie et d'Angeiologie, pp. 447–452, 1986.
Ametani et al "Importance of Glutathione and Adenoseine in Cold Storage of the Kidney", Transplantation Proceedings 22(2); 469–471 Apr. 1990.
Fuller et al Chem Abst 105(1); 4240 1986.

*Primary Examiner*—Raymond Henley, III
*Attorney, Agent, or Firm*—Larson and Taylor

[57] ABSTRACT

Perfusion and preservation and/or reperfusion solutions for surgery and organ transplantation, including that of the heart, a feature of which solutions is the inclusion of at least one antioxidant compound, such as a trapping agent for free oxygen radicals, in particular glutathione in the reduced state or N-acetylcysteine, said solutions possessing a zero or greatly reduced partial pressure of oxygen which is maintained substantially at this value up to the time of use. The solution is preferably presented in flexible bags impermeable to oxygen.

7 Claims, No Drawings

SOLUTIONS FOR THE PERFUSION, PRESERVATION AND REPERFUSION OF ORGANS

This application is a continuation of application Ser. No. 07/946,073 filed Sep. 18, 1992, now abandoned which is a continuation-in-part of U.S. application Ser. No. 07/794,878, filed Nov. 19, 1991, now abandoned.

The present invention relates to solutions for the perfusion, preservation (or storage) and/or reperfusion of organs, including those employed in heart transplantation. It also relates to a method for using these solutions applied in the different phases of a transplantation.

One of the main causes of failure of heart transplants originates from the risks of degradation, or even of necrosis, of the graft, which manifest themselves during reoxygenation of the transplanted organ and which are linked to the ischemia, generally prolonged, occurring between initiation of the explantation from the donor and completion of the implantation in the recipient.

An ischemia of four to five hours constitutes, for example in the case of the heart, the upper tolerable limit, and does not rule out a large number of accidents.

To limit this risk, many authors have proposed and used protective solutions, both for perfusion of the organ to be explanted and for its preservation at low temperature and its reperfusion during transplantation.

Examples of these solutions are the following solutions:

Bretschneider's HTK

Collins

St. Thomas

UW

Stanford

These solutions, however, possess only limited advantages, and afford at most only a partial protection against the risks which appear during reperfusion, and which are attributed in part to the metabolic production of free oxygen radicals produced in copious amounts, in particular during reoxygenation of the ischemic organ.

The risk of oxidative cell and membrane degradations originating from the production of these radicals has been the subject of several studies in the field of myocardial protection by cardioplegia. These various investigations have suggested the introduction into the protective solutions used of substances capable of counteracting the production or the effect of free radicals, and in particular antioxidant substances. Various compounds have been proposed, some, such as deferoxamine, allopurinol, catalase and peroxidase, as being capable of counteracting free radical production, others such as superoxide dismutase being capable of destroying these radicals, yet others such as vitamin E or equivalent (Trolox) being capable of "neutralizing" the free radicals.

These latter compounds also include molecules bearing thiol groups, such as N-acetylcysteine or reduced glutathione (GSH), which has been considered to be a free-radical "trapping" agent (scavenger). However, the literature is divided on the value of glutathione.

Thus, G. W. Standeven et al., in J. Thorac. Cardiovasc. Surg. 1979, 78,893–907 Cold-Blood potassium cardioplegia, found little difference in the level of protection afforded by the addition of glutathione.

In contrast, M. Bernlet et al., in Reperfusion-induced Arrhythmias and Oxygen-derived Free Radicals, Circulation Research, Vol. 58, no. 3, March 1986, 331–340, find that the addition of L-methionine, superoxide dismutase, catalase, mannitol, glutathione or deferoxamine to the perfused isolated rat heart reduces the risk of fibrillation or of ventricular tachycardia during reperfusion.

J. C. Chatham et al., in Depletion of Myocardial Glutathione: Its effects on heart function and metabolism during ischaemia and reperfusion, Cardiovascular Research, 1988, 22, 833–839, concludes that a depletion of glutathione during ischemia of rat hearts does not appear to result in a worsening of the metabolic impairment.

A. Blaustein et al., in Myocardial Glutathione Depletion Impairs Recovery After Short Periods of Ischaemia, Circulation, Vol. 80, no. 5, November 1989, conclude that a depletion of glutathione in the isolated rat heart, obtained by injection of diethyl maleate, leads to a poor recovery of systolic function, and that an improvement may be obtained in the case of reperfusion with a solution supplemented with glutathione.

A. Singh et al., in Relation Between Myocardial Glutathione Content and Extent of Ischaemia—Reperfusion Injury, Circulation, Vol. 80, no. 6, December 1989, 1795–1803, show an increase in the GSH content in pigs perfused intravenously with glutathione five minutes before and during cardiac reperfusion, and find an improvement in the local recovery.

W. N. Wicomb et at., in Role of Glutathione in 24-hour Heart Storage by Microperfusion Using a New Polyethylene Glycol Solution, J. Mol. Cell. Cardiol. 22 (Supplement V) 1990, p. 82, report an improvement in the recovery of the isolated rabbit heart preserved in a protective solution comprising GSH glutathione, the simple addition of glutathione during reperfusion not being effective.

V. Kantamneni et al., in Extended Preservation of Canine Myocardium Using UW Solution, J. Mol. Cell. Cardiol. 1990 (Suppl. V); 22:22 (Abstr), conclude that solutions (UW solutions and modified UW solutions) containing glutathione, which show some degree of efficacy in the preservation of isolated organs such as liver, kidney and pancreas, do not bring about significant improvements compared to modified Collins solution not containing this compound, and that these solutions were unable to permit a significant increase in the period of preservation of the heart in dogs.

The addition of N-acetylcysteine is studied by M. B. Forman, Glutathione Redox Pathway and Reperfusion Injury, Circulation, Vol. 78, no. 1, July 1988, 202–213. He suggests that a treatment with N-acetylcysteine (NAC) before reperfusion can improve postischemic recovery.

While it may hence appear advantageous to use substances acting against the production or the effect of free radicals in the myocardium in the context of cardioplegic protection, the choice of compound and the procedure for its use do not appear to be obvious, and the addition of these compounds, including glutathione, to myocardial perfusion and reperfusion solutions in daily hospital practice has failed to yield decisive results.

Ph. Menasché et al., in les Piégeurs de Radicaux Libres dans la Protection Myocardique en Chirurgie Cardiaque [Free-Radical Trapping Agents in Myocardial Protection in Cardiac Surgery], Ann. Cardiol. Angéiot; 1986, 35 (no. 7bis), 447–452, conclude, however, that the preservation of postischemic left ventricular function, due to a given cardioplegic solution, could be significantly improved by adding antioxidants capable of preventing the formation of free radicals or of destroying or neutralizing them. In contrast, the choice of the most effective antioxidant from among the many candidates, including superoxide dismutase SOD, peroxidase and glutathione, is not obvious, not to mention the possible side effects or toxic effects. A fortiori, when we turn from the field of cardioplegia, in which the periods of ischemia are relatively short, to the field of transplantation, the literature provides no genuinely useable information about the choice and procedure for use of genuinely effective protective solutions.

In WO 88/05044 another way is suggested, using nitroxide compounds for the prophylaxis and treatment of ischemic cell damage, during perfusion, preservation or reperfusion of organs in cases of cardioplegia or organ transplantations, even if other types of low-molecular free radical scavengers may be added, as for instance aliphatic or aromatic thiols or alcohols. The nitroxides may be employed as stable free radicals or in the reduced form and the compound may be packaged in an ampoule under an inert atmosphere or in vacuo so that when to be used it may be reconstituted in a physiologically acceptable buffer.

In U.S. Pat. No. 4,877,810, the Trolox derivative of vitamin E, is suggested as a very efficacious means, instead of superoxide dismutase (SOD) for prevention or reclusion of heart tissue damage upon reperfusion in cardiovascular surgery, including heart transplants. Ascorbic acid is preferably added, to prevent oxydation of Trolox, where ascorbic acid may be replaced, for the same purpose, by thiol compounds, including glutathione.

In these documents it is deemed that thiol antioxydant compounds, including gluthatione, are not the best choice for protection- against oxydative damage of organs and, in accordance with the other discussed prior art, the state of oxydation of glutathione is not considered as being critical.

An objective of the present invention is to solve these problems and to provide exceptionally effective protective solutions for the preservation of organs for the purpose of surgical operations and especially of transplantation. The organs in question comprise the heart, as well as the other organs, and in particular the liver, lung and kidney.

The present invention provides, to this end, for a perfusion and storage solution for the explanted organ and a reperfusion solution for the organ undergoing implantation, a feature of both solutions being the inclusion of at least one antioxidant triol compound which can be a trapping agent for free oxygen radials, said solutions possessing a zero or greatly reduced partial pressure of oxygen which is maintained substantially at this value up to the time of use.

Preferred thiols include glutathione in the reduced state (GSH) or its precursors or related Substances, and in particular N-acetylcysteine (NAC), glutathione analogs and in particular glutathione monoester.

Other compounds containing a thiol function may be used, in particular diethyldithiocarbamate, its analogs and derivatives, as well as converting enzyme inhibitors.

According to the invention, the solutions are prepared and stored protected from aerial oxygen, being, for example, prepared in the form of outgassed solutions, preferably under a nitrogen atmosphere. The storage and preservation of the solutions according to the invention are carried out in airtight containers such as bottles or, preferably, airtight bags made of plastic, for example made of laminated composites of a type known per se.

In one embodiment the solution is stored, as a whole, in the container. In another embodiment the thiol, preferably glutathione, is separately stored in the reduced state in the container under reduced partial pressure of oxygen, for example in an airtight syringe, which allows injection of the content of the syringe into a plastic bag containing the other components of the solution, just before use, as it was discovered that hypothermic storage conditions in usual bags during periods up to 3 hours result in an only minimal rate of glutathione oxydation.

Advantageously, the solutions according to the invention can also contain, apart from free-radical inhibitory thiols, a compound counteracting radical formation, such as metal chetators and especially deferoxamine (INN).

Reduced value of the oxygen concentration according to the invention is preferably understood to mean a maximum concentration of dissolved oxygen of less than 0.1 ppm.

In the case where glutathione is used, the reduced glutathione content of the solution is preferably of the order of 0.5 to 10, and advantageously of the order of 3, mmol/l. In the case where the thiol is NAC, the content is preferably of the order of 10 to 80, and advantageously of the order of 40, mmol/l.

The invention is preferably implemented in different forms, depending on whether it is applied to the perfusion and preservation of the explanted organ, or to the reperfusion of the implanted organ.

In the case of a perfusion and preservation preparation according to the invention, the solution is made up so as to prevent the formation of cell edema and the appearance of oxidative lesions while limiting the calcium overload. Furthermore, for some organs, and in particular the heart, the solution is capable of playing the part of a metabolic inhibitor.

Advantageously, the calcium content is low, preferably below 0.5 mM, and it is preferable for the solution to contain magnesium, preferably at a content above 10 mM. In addition, a lower pH, in particular 7.40±0.40, is preferred. In the case where the perfusion and preservation solution is intended for the heart, a potassium concentration preferably equal to at least 10 mM is provided, it being possible for the potassium, where appropriate, to be absent for the other organs.

In an especially effective and advantageous embodiment of the invention, a solution for the perfusion and preservation (storage) of the heart according to the invention contains the following compounds:

| A Perfusion and storage solution (1) | |
|---|---|
| Constituent | Concentration (mmol/liter) |
| $K^+$ | 10–30 |
| $Na^+$ | 90–120 |
| $Mg^{++}$ | 10–20 |
| $Ca^{++}$ | 0.005–1.2 |
| $Cl^-$ | 100–160 |
| Mannitol | 50–200 |
| Glutamate | 4–26 |
| NAC | 10–80 |
| or GSH | 0.2 to 0.5–10 |
| Osmolarity | 270–450 (for example 370) mOsm/l |
| pH | 7.40 ± 0.40 (at 20° C.) |

In the case of a reperfusion preparation according to the invention, the solution is made up so as to continue to limit cell edema and oxidative lesions. It is also contrived so as to reestablish calcium homeostasis. The preferred pH is 7.70±0.30. In the case of the heart, it is made up so as to prolong metabolic inhibition, and will retain potassium at a concentration preferably above 10 mM.

Thus, in an advantageous embodiment, the reperfusion solution contains the following compounds:

| B Reperfusion solution (2) | |
| --- | --- |
| Constituent | Concentration (mmol/liter) |
| $K^+$ | 10–30 |
| $Na^+$ | 90–120 |
| $Mg^{++}$ | 0–20 |
| $Ca^{++}$ | 0.005–1.2 |
| $Cl^-$ | 100–160 |
| Mannitol | 50–200 |
| Glutamate | 4–26 |
| NAC | 10–80 |
| or GSH | 0.2 to 0.5–10 |
| Osmolarity | 270 to 450 (for example 370) mOsm/l |
| pH | 7.70 ± 0.30 at 28° C. |

The preferred embodiment of the perfusion and preservation solution is:

| C Perfusion and storage solution (1) | |
| --- | --- |
| Constituent | Concentration (mmol/liter) |
| $K^+$ | 12 |
| $Na^+$ | 100 |
| $Mg^{++}$ | 13 |
| $Ca^{++}$ | 0.25 |
| $Cl^-$ | 110.4 |
| Mannitol | 109.8 |
| Glutamate | 20 |
| GSH | 0.5 to 3 |
| Osmalarity | 370 mOsm/l |
| pH | 7.40 (at 20° C.) | and the preferred embodiment of the reperfusion solution is

| D Reperfusion solution (2) | |
| --- | --- |
| Constituent | Concentration (mmol/liter) |
| $K^+$ | 14.9 |
| $Na^+$ | 100 |
| $Mg^{++}$ | — |
| $Ca^{++}$ | 1.2 |
| $Cl^-$ | 97.5 |
| Mannitol | 136 |
| Glutamate | 20 |
| GSH | 0.5 to 3 |
| Osmolarity | 370 mOsm/l |
| pH | 7.70 at 28° C. |

Naturally, the compounds thus defined may be replaced by compounds having equivalent functions, the molar contents preferably remaining substantially unchanged.

Thus, glutamate, whose function is to stimulate anaerobic energy production by myocardial cells, may be replaced, in particular, by aspartates, succinates, fumarates and malates.

Mannitol, an impermeant compound whose function is to limit edema, may be replaced by other substances playing the part of an impermeant compound in the interstitial medium, increasing osmotic pressure, such as lactobionate (by reducing proportionately the chloride concentration), raffinose or sucrose. Since the chosen impermeant substance must not be metabolized or taken up by the organ, mannitol is suitable for the heart whereas it will be ruled out for the liver.

The relatively acid pH of the perfusion and preservation solution, preferably of the order of 7.40 at 28° C., is preferably produced without a buffer.

The pH of the reperfusion solution, preferably adjusted to 7.70 at 28° C., may be optionally produced using a buffer (in particular bicarbonate, histidine).

Preferably, the two solutions according to the invention are presented, in a single package, in the form of one or more containers per solution, preferably deformable bags having airtight walls, of total volume 1500 to 2000 ml.

According to a further improvement of the invention there is provided a unique solution for the perfusion, preservation and reperfusion of the heart which can be used during all the phases of a transplantation procedure as a cardioplegic solution for arresting the donor heart, as a storage medium during the hypothermic transportation and during its implantation, either in its cristalloid form or preferentially, after having diluted it with blood. This solution contain the following compounds.

| E | | |
| --- | --- | --- |
| | Concentration | |
| Constituent (e.g. in a 2 l bag) | g/l | mmol/liter |
| $K^+$ | | 15 ± 5% |
| $Na^+$ | | 100 ± 10% |
| $Mg^{++}$ | | 13 ± 5% |
| $Ca^{++}$ | | 0.25 ± 5% |
| Chlorides | | 41.5 ± 5% |
| calcium chloride, $2H_2O$ | 0.037 | |
| potassium chloride | 1.118 | ± 5% |
| magnesium chloride | 2.642 | |
| Histidine (base form) | 4.650 | 30 ± 10% |
| Mannitol | 10.930 | 60 ± 5% |
| Lactobionate (acid form) | 28.664 | 80 ± 5% |
| Glutamate (acid form) | 2.942 | 20 ± 10% |
| Water (quantity for one liter volume adjusted to pH 7.30 ± 0.10 at +20° C.) | | |
| Theorical osmolality 360 m Osm/kg | | |
| In a e.g. 10 ml syringe | | |
| Glutathione (reduced GSH) | 185.4 | 600 ± 10% |
| Histidine | 4.650 | 30 ± 10% |
| Water (quantity for 1 l adjusted at pH 7.30 ± 0.10 at +20° C.) | | |

In this solution prevention of Calcium overload in the cells is secured by the presence of the glutamate component which has the capacity of yielding ATP under anaerobic conditions, the low calcium concentration which reduces entry by passive diffusion, the high sodium concentration which limits the sodium-calcium exchange, where entry of calcium through voltage-dependent channels is limited by the low potassium concentration and the amount of magnesium. This extracellular type of ionic formulation is made possible by the concomitant presence of effective impermeants. Mannitol has the dual capacity to behave as an osmotic agent and a free radical scavenger. Lactobionate affords a more effective prevention of cell swelling than mannitol alone and the total concentration of impermeants is equivalent to that of intracellular proteins and impermeable anions which exert a driving force from the outside to the inside of the cells.

The pH is preferably slightly acid (7.20–7.40) as it was discovered that this value further enhances prevention of calcium overload and further that on the contrary of more alkaline values, it adds to cell protection during hypothermic ischemic arrest.

The solution is buffered with histidine because it has been discovered that among buffers available for human use, histidine is the only one which remains operative at low temperatures.

Preferably the volume ratio of syringe/bag is about 1/200.

During the preparation of this unique solution, care should be taken to sterilize separately the histidine and the lactobionate, for example by adding sterilized histidine to the previously sterilized solution containing the other components of the bag.

The subject of the invention is also a method for using the solutions according to the invention for heart transplantation, wherein cardiac arrest of the organ to be explanted is induced by perfusion of the perfusion and preservation solution for a few minutes, wherein the organ removed is placed in a container, bag or bottle filled with said solution protected from the air for preservation at low temperature, wherein the organ is perfused again using said solution during the grafting of the transplanted heart, and wherein the graft is then reperfused after the graft has been installed, this time using the reperfusion solution according to the invention, for a period preferably of the order of 5 minutes, after which the systemic circulation is reestablished.

The subject of the invention is also a method of use for the transplantation of organs other than the heart, and in particular liver, kidney and lung, wherein perfusion of the organ to be explanted is performed for a few minutes with the perfusion and preservation solution, the subsequent operations of preservation and reperfusion being similar to those in the abovementioned case of the heart.

Other advantages and features of the invention will become apparent on reading the description which follows, given as an example without implied limitation.

1. Preparation of the perfusion and preservation solution

An outgassed, sterile, pyrogen-free aqueous medium is prepared under conditions of protection from atmospheric oxygen, and having the composition C.

This composition possesses on average a maximum concentration of dissolved oxygen<0.1 ppm and a pH of 7.40 at 20° C. This solution is packaged in plastic bags impermeable to atmospheric oxygen, or in plastic bags which are permeable to oxygen but are themselves contained in a bag of a plastic/aluminum complex which is impermeable to atmospheric oxygen.

2. Preparation of the reperfusion solution

Taking the same precautions as in Example 1, a reperfusion solution having the composition D is prepared.

This composition can contain a bicarbonate or histidine buffer maintaining the pH at 7.70 at 28° C.

This solution is placed in similar bags of volume 100 ml.

3. Test of solutions containing NAC on isolated rat heart preparations

Fifty isovolumic preparations of isolated hearts from Sprague-Dawley rats weighing 300 grams were used, the hearts being connected rapidly to a non-recirculating Langendorff perfusion column to establish a retrograde perfusion using an oxygenated (95% $O_2$, 5% $CO_2$) Krebs-Henseleit buffer, to establish a retrograde perfusion at a pressure of 100 cm of water. The left ventricular pressure, its derivative and the end-diastolic pressure were recorded continuously. The coronary flow rate was measured by noting the venous coronary flow rate. Left ventricular stimulation was maintained at a frequency of 320/min.

After a twenty-minute monitoring period, thirty hearts were arrested by perfusion using the preservation and perfusion solution at 4° C., and then rapidly placed in glass containers filled with the same solution and surrounded by ice. The hearts were maintained therein for five hours, with a mean myocardial temperature of 2° C. at the end of storage. The hearts were then reconnected to the perfusion circuit and subjected to an additional ischemia for one hour at between 15° and 18° C. The hearts were divided into three groups, including a control group which received a first perfusion of a solution which was identical but devoid of NAC on establishment of the post-storage ischemia and an additional perfusion of 25 ml of this solution immediately before unclamping the aorta, the perfusions being performed at 4° C. and 28° C., respectively. The same protocol was observed for the second group of hearts, except for the fact that the solution contained 0,04 M NAC. In the third group, a solution containing NAC at 28° C. was distributed in a single dose at the end of the ischemia. In this latter group, the NAC concentration was adjusted to 0.072 M so that all the hearts treated received the same amount of this substance, that is to say approximately 1.80 millimoles. The bottles containing the solutions as well as the connecting tubes were protected from light in order to avoid oxidation. In all three groups, the perfusions after storage were delivered at a pressure of 30 cm of water. After a period of ischemia of six hours, the hearts were reperfused for one hour at 37° C.

For all three groups, the stimulation was stopped and the left intraventricular balloon deflated during the period of ischemia so as to simulate clinical conditions. After reperfusion, stimulation was reestablished. Isovolumetric measurements of the coronary flow rate, the left ventricular pressure, its first derivative and the telediastolic pressure were performed three times during the monotoring period and then at 5, 30, 45 and 60 minutes during the reperfusion.

The results were as follows:

Coronary flow rate: after sixty minutes of reperfusion, the flow rate of all the hearts was reduced significantly ($p<0.001$) relative to the pre-ischaemic reference values. However, the best recovery of coronary flow rate was noted in the groups treated with NAC (Table I).

Left ventricular function: the left ventricular pressure decreased significantly after the ischemia and reperfusion in the hearts of all three groups (Table I). However, the hearts of the control group (Group I) and those which had received only the reperfusion supplemented with NAC at the end of the ischemic episode after storage (Group III) manifested significantly greater pressure losses ($p<0.001$) than those protected with the multidose solution enriched with NAC (Group II) during the last hour of overall ischemia ($p<0.01$). In addition, throughout the reperfusion period, a significantly greater pressure was developed in Group II. The effects of the treatment on the postischemic derivative dP/dt were similar to those for the pressure developed, and the largest values were obtained for Group II.

Left ventricular diastolic pressure: at the end of the arrest-storage-ischemia protocol, the hearts of the control Group I as well as those of Group III underwent a significant loss of compliance. In contrast, postischemic contracture was significantly decreased in Group II.

The results of this experiment demonstrate the substantial advantage of using the protective solutions according to the invention in a realistic model capable of extrapolation to the sphere of human transplantation.

4. Tests of solutions containing GSH on isolated rat heart preparations

The tests are conducted on rat heart preparations, with isovolumetric contraction, divided into three groups 1, 2 and 3. Cardiac arrest is obtained by perfusion of the perfusion and storage solution at +4° C. The hearts are then stored by immersion for 5 h in the solution at +2° C. A one-hour period of ischemia at 15°– 18° C. is then established, with initial perfusion with administration of the perfusion and storage solution at the beginning of this period of ischemia, and administration of the reperfusion solution at the end of the hour of ischemia, that is to say immediately before unclamping the aorta. The temperatures of the solutions are 4° and 28° C., respectively. They are administered under a pressure of 30 cm $H_2O$. After the period of ischemia, the hearts are reperfused for one hour at 37° C.

The solutions used are as follows: Group 1 (control): solution identical to the solution C but devoid of GSH, then solution D devoid of GSH, Group 2: solution C, then solution D, Group 3: solution D supplemented with deferoxamine, then solution D supplemented with deferoxamine.

The results are recorded in Table II. They show the spectacular improvement produced by the solutions C, distinguished by the presence of GSH and the low oxygen concentration.

In the table:
CF= coronary flow rate (ml/min),
Pdiast= diastolic pressure (mm Hg),
Pdev= pressure developed (nun Hg),
dP/dt= first derivative of the pressure (mm Hg. sec$^{-1}$).

5. Use of the solutions in human heart transplantation

The solutions are prepared according to Examples 1 and 2. After the establishment of transthoracic access to the explanted heart, 1000 to 2000 ml of the solution C at 4° C. are perfused into the heart via the aorta for three to four minutes. The heart is removed, then installed in a jar provided for this purpose so as to be immersed in the solution C, and the jar is cooled to the customary preservation temperature of +4° C.

When the graft has been transported to the prepared recipient maintained by means of an extracorporeal circulation, grafting of the heart is carried out and, during this operation, an antero- or retrograde perfusion of the solution C is performed at +4° C. in order to reinforce cardiac arrest. The perfusion volume is generally of the order of 1000 to 2000 ml.

When installation of the graft is complete, the heart is reperfused via the aorta using the solution D at 28°–37° C. for a period of 5 rain on average, the volume used being of the order of 1000 ml. At the end of this perfusion, the aorta is unclamped, circulation is reestablished and severing of the extracorporeal circulation is performed in the customary manner.

TABLE II

A. Analysis of variance (I) CF (ml/min) (n = 7)

1) Group 1 = 12.6 ml/min ± 0.5 ml/min.
2) Group 2 = 14.2 ± 0.4 ml/min.
3) Group 3 = 10.6 ± 0.4 ml/min.
Row (line) effect         F > 19,1173 => p < 0.001
Column (time) effect      F > 6.3592 => p < 0.001
(1) versus (3) p < 0.01
(2) versus (3) p < 0.001

(II) Pdiast (mmHg) (n = 7)

1) Group 1 = 33.1 ± 2.9 mmHg
2) Group 2 = 16.9 ± 1.4 mmHg
3) Group 3 = 21.7 ± 2.2 mmHg
Line effect              = F > 13.1426 p < 0.001
Time effect              = N.S.
(1) versus (2) p < 0.001
(1) versus (3) p < 0.01
(2) versus (3) N.S.

(III) Pdev (mmHg) (n = 7)

Group 1 = 84.0 ± 3.0 mmHg
Group 2 = 104.5 ± 4.1 mmHg
Group 3 = 116.8 ± 3.6 mmHg
Line effect              F > 20.6411 p < 0.001
Time effect              N.S.
(1) versus (2) p < 0.001
(1) versus (3) p < 0.001
(2) versus (3) N.S.

(IV) dP/dtmax (+) (n = 7)

Group 1 = 2932 ± 96 mmHg sec$^{-1}$
Group 2 = 3418 ± 122 mmHg sec$^{-1}$
Group 3 = 3479 ± 173 mmHg sec$^{-1}$
Line effect              F > 4.7966 p < 0.01
Time effect              N.S.
(1) versus (2) p < 0.05
(1) versus (3) p < 0.05
(2) versus (3) N.S.

B. Scheffé test at 60 min of reperfusion (I) CF (ml/min) (n = 7)

Group 1 = 11.3 ± 0.8 ml/min.
Group 2 = 12.6 ± 0.8 ml/min.
Group 3 = 8.9 ± 0.7 ml/min.
(1) versus (3) N.S.
(2) versus (3) p < 0.02

(II) Pdiast (mmHg) (n = 7)

Group 1 = 30.4 ± 5.0 mmHg

TABLE I

Effect of NAC on coronary flow rate and left ventricular pressure developed

| Group | Coronary flow rate (ml/min) | | Left ventricular pressure developed (mm Hg) | |
|---|---|---|---|---|
| N = 10 | Normal | Reperfusion | Normal | Reperfusion |
| Control Solution without NAC | 14.6 ± 0.8 | 10.5 ± 0.4 | 130.7 ± 2.1 | 63.6 ± 3.3 |
| Second group (0.04 M) NAC | 14.8 ± 0.6 | 12.1 ± 0.5* | 126.4 ± 2.8 | 101.5 ± 3.4*** |
| Third group (0.07 M) NAC | 16.0 ± 0.5 | 13.4 ± 0.4** | 129.7 ± 2.0 | 69.8 ± 3.6 |

*p < 0.05 with respect to the reference cardioplegia.
**p < 0.01 with respect to the reference cardioplegia.
***p < 0.001 with respect to the reference cardioplegia and the reperfusion enriched with NAC.

TABLE II-continued

Group 2 = 14.9 ± 1.9 mmHg
Group 3 = 19.6 ± 4.0 mmHg
(1) versus (2) p < 0.05
(1) versus (3) N.S.
(2) versus (3) N.S.
(III) Pdev (1) mmHg (n = 7)

Group 1 = 80.1 ± 5.3 mmHg
Group 2 = 107.6 ± 8.5 mmHg
Group 3 = 120.7 ± 8.9 mmHg
(1) versus (2) p < 0.05
(1) versus (3) p 4 0.01
(2) versus (3) N.S.
(IV) dP/dt max (mmHg $sec^{-1}$) (n = 7)

Group 1 = 2714 ± 110 mmHg $sec^{-1}$
Group 2 = 3429 ± 260 mmHg $sec^{-1}$
Group 3 = 3500 ± 300 mmHg $sec^{-1}$
(1) versus (2) p < 0.05
(1) versus (3) p < 0.05
(2) versus (3) N.S.
C. Comparison of the reference values with the values measured after 60 min of reperfusion (Student's test)

(I) CF (ml/min)

Group 1 = 14.4 ± 0.7 v 11.3 ± 0.8 ml/min p 0.05
Group 2 = 15.0 ± 0.4 v 12.6 ± 0.8 ml/min p 0.05
Group 3 = 15.1 ± 0.3 versus 8.9 ± 0.7 ml/min p 0.001
(II) Pdiast (mmHg)

(1) 11.3 ± 0.7 versus 30.4 ± 5.0 mmHg p < 0.01
(2) 10.6 ± 0.7 versus 14.9 mmHg ± 1.9 N.S.
(3) 9.6 ± 0.5 versus 19.6 ± 4.0 mmHg p < 0.05
(III) Pdev (mmHg)

Group 1 = 132.1 ± 3.1 versus 80.1 ± 5.3 mmHg p < 0.001
Group 2 = 134.4 ± 2.7 versus 107.6 ± 8.5 mmHg p < 0.05
Group 3 = 149.3 ± 2.9 versus 120.7 ± 8.9 mmHg p < 0.05
(IV) dP/dt max (mmHg $sec^{-1}$)

(1) 4281 ± 147 versus 2714 ± 110 mmHg $sec^{-1}$ p < 0.001
(2) 4714 ± 200 versus 3429 ± 260 mmHg $sec^{-1}$ p < 0.01
(3) 4191 ± 289 versus 3500 ± 300 mmHg $sec^{-1}$ N.S.

I claim:

1. In the perfusion, preservation or reperfusion of the heart by delivering to the heart a perfusion, preservation or reperfusion solution, the improvement comprising employing as said solution a solution consisting essentially of the following formulation:

| Constituent | Concentration g/l | Concentration mmol/liter |
| --- | --- | --- |
| K+ | | 15 ± 5% |
| Na+ | | 100 ± 10% |
| Mg++ | | 13 ± 5% |
| Ca++ | | 0.25 ± 5% |
| Chlorides | | 41.5 ± 5% |
| calcium chloride 2H$_2$O | 0.037 | |
| potassium chloride | 1.118 | ± 5% |
| magnesium chloride | 2.642 | |
| Histadine base form | 4.650 | 30 ± 10 |
| Mannitol | 10.930 | 60 ± 5% |
| Lactobionate base form | 28.664 | 80 ± 5% |
| Glutamate acid form | 2.942 | 20 ± 10% |
| GSH | | 3 ± 10% |
| Histidine | | 0.15 ± 10% |

Water quantity for 1 liter adjusted at pH 7.30 ± 0.10 at +20° C.

wherein said solution optionally has a maximum concentration of dissolved oxygen of 0.1 ppm or less.

2. In the perfusion, preservation or reperfusion of the heart by delivering to the heart a perfusion and preservation solution, the improvement comprising employing as said solution a solution consisting essentially of the following formulation:

| Constituent | Concentration mmol/liter |
| --- | --- |
| K+ | 10–30 |
| Na+ | 90–120 |
| Mg++ | 10–20 |
| Ca++ | 0.005–1.2 |
| Cl- | 100–160 |
| Mannitol | 50–200 |
| Glutamate | 4–26 |
| NAC | 10–80 |
| or GSH | 0.2 to 0.5–10 |
| Osmolarity | 270–450 mOsm/l |
| pH | 7.40 ± 0.40 at 20° C. |

3. An improvement according to claim 2 in which the solution is a perfusion and preservation solution of the following formulation:

| Constituent | Concentration mmol/liter |
| --- | --- |
| K+ | 12 |
| Na+ | 100 |
| Mg++ | 13 |
| Ca++ | 0.25 |
| Cl- | 110.4 |
| Mannitol | 109.8 |
| Glutamate | 20 |
| GSH | 0.5 to 3 |
| Osmolarity | 370 mOsm/l |
| pH | 7.40 at 20° C. |

4. In the perfusion, preservation or reperfusion of the heart by delivering to the heart a perfusion, preservation or reperfusion solution, respectively, comprising employing as said solution a solution comprising an efficient concentration of free-radical trapping agent selected from the group consisting of glutathione in the reduces state (GSH) and N-acetyleysteine (NAC), wherein said agent is substantially protected from oxidation, said solution having a pH of 7.30±0.10 at +20° C., said solution further comprising:

K+ at a concentration of 15±5% mmol/l
Na+ at a concentration of 100±10% mmol/l
Mg++ at a concentration of 13±5% mmol/l
Chlorides at an efficient concentration
an efficient concentration of at least one impermeant compound preventing the formation of cell edema.

5. A method according to claim 4 wherein said pH of 7.30±0.10 at +20° C. is obtained by a histidine buffer.

6. In the perfusion, preservation or reperfusion of the heart with a reperfusion solution, the improvement comprising using as said solution a solution consisting essentially of the following formulation:

| Constituent | Concentration mmol/liter |
| --- | --- |
| K+ | 10–30 |
| Na+ | 90–120 |
| Mg++ | 10–20 |
| Ca++ | 0.005–1.2 |

-continued

| Constituent | Concentration mmol/liter |
|---|---|
| Cl⁻ | 100–160 |
| Mannitol | 50–200 |
| Glutamate | 4–26 |
| NAC | 10–80 |
| or GSH | 0.2 to 0.5–10 |
| Osmolarity | 270–450 mOsm/l |
| pH | 7.70 ± 0.30 at 20° C. |

7. In the reperfusion of the heart by delivering to the heart a reperfusion solution, the improvement comprising using as said solution a solution of the following formulation:

| Constituent | Concentration mmol/liter |
|---|---|
| K⁺ | 14.9 |
| Na⁺ | 100 |
| Mg⁺⁺ | — |
| Ca⁺⁺ | 1.12 |
| Cl⁻ | 97.5 |
| Mannitol | 136 |
| Glutamate | 20 |
| GSH | 0.5 to 3 |
| Osmolarity | 370 mOsm/l |
| pH | 7.70 at 20° C. |

* * * * *